United States Patent [19]

Ishihara et al.

[11] 4,339,397

[45] Jul. 13, 1982

[54] METHOD FOR THE PREPARATION OF A SODIUM SALT OF 1-ALKYNE COMPOUND

[75] Inventors: Toshinobu Ishihara; Kenichi Taguchi; Akira Yamamoto, all of Joetsu, Japan

[73] Assignee: Shin-Etsu Chemical Co., Ltd., Tokyo, Japan

[21] Appl. No.: 209,266

[22] Filed: Nov. 21, 1980

[30] Foreign Application Priority Data

Nov. 26, 1979 [JP] Japan ............................... 54-152819

[51] Int. Cl.³ ............................................. C07F 1/04
[52] U.S. Cl. ............................................. 260/665 R
[58] Field of Search ................................. 260/665 R

[56] References Cited

U.S. PATENT DOCUMENTS

3,975,453 8/1976 Smith ........................... 260/665 R

OTHER PUBLICATIONS

Kirk Othmer Encyclopedia of Chem. Technology, Interscience Encyclopedia Inc., N.Y., vol. 7 (1951 Ed.).

Primary Examiner—Helen M. S. Sneed
Attorney, Agent, or Firm—Toren, McGeady & Stanger

[57] ABSTRACT

The invention provides a novel and improved method for the preparation of a sodium salt of a 1-alkyne of the general formula

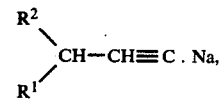

in which $R^1$ and $R^2$ are each a hydrogen atom or a monovalent hydrocarbon group free from aliphatic unsaturation, by the reaction of a corresponding 1,2-alkadiene with metallic sodium in an inert organic solvent. According to the invention, the metallic sodium is dispersed in the inert solvent as finely as possible to have a particle diameter not exceeding 1000 μm so as that the reaction velocity is very much increased even under atmospheric pressure to give an improved yield of the product.

4 Claims, No Drawings

METHOD FOR THE PREPARATION OF A SODIUM SALT OF 1-ALKYNE COMPOUND

BACKGROUND OF THE INVENTION

The present invention relates to a method for the preparation of a sodium salt of 1-alkyne or, more particularly, to a method for the preparation of a sodium salt of 1-alkyne represented by the general formula

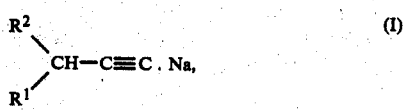

in which R and R$^2$ each denote a hydrogen atom or a monovalent hydrocarbon group having no aliphatic unsaturation, by the reaction of a 1,2-alkadiene of the formula

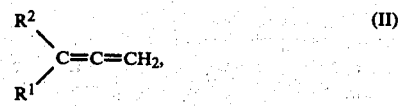

in which R$^1$ and R$^2$ each have the same meaning as defined above, with metallic sodium.

In the prior art, it is well known that a sodium salt of 1-alkyne of the above general formula (I), which is a useful intermediate for the synthetic preparation of various organic compounds such as 1-alkynes, can be prepared by the reaction of a corresponding 1,2-alkadiene of the general formula (II) above with metallic sodium. For example, 1,2-butadiene is reacted with metallic sodium of wire-like form in an inert reaction medium under a superatmospheric pressure, e.g. 10 to 20 kg/cm G, to give butynyl sodium (see, for example, Japanese patent Disclosure No. 50-18406). This method is necssarily carried out in a pressurized vessel, e.g. autoclave, because the reaction is carried out under a superatmospheric pressure. Further, the reaction velocity in the above known method is relatively low and the yield of the desired butynyl sodium rarely exceeds 50% based on the 1,2-butadiene used in the reaction.

SUMMARY OF THE INVENTION

It is an object of the present invention to provide a novel and improved method for the preparation of a sodium salt of a 1-alkyne of the above general formula (I) by the reaction of a 1,2-alkadiene of the formula (II) with metallic sodium, according to which the reaction can be carried out under atmospheric pressure with an improved reaction velocity to give a remarkably high yield of the desired compound.

Thus, the method of the present invention for the preparation of the sodium salt of a 1-alkyne of the general formula (I) comprises reacting a 1,2-alkadiene of the general formula (II) with metallic sodium in an inert solvent, in which the metallic sodium is added to the reaction mixture in a finely divided particulate form having a particle diameter not exceeding 1000 $\mu$m or, preferably, not exceeding 500 $\mu$m.

By the above method, the reaction proceeds rapidly even under atmospheric pressure to give the desired product in a quantitative yield.

DETAILED DESCRIPTION OF THE PREFERRED EMBODIMENTS

The 1,2-alkadiene compound as the starting reactant of the inventive method is expressed by the above given general formula (II), in which R$^1$ and R$^2$ are each independently a hydrogen atom or a monovalent hydrocarbon group having no aliphatic unsaturation as exemplified by alkyl groups such as methyl and ethyl groups, aryl groups such as phenyl group and aralkyl groups such as benzyl group.

Particular examples of the 1,2-alkadienes applicable to the inventive method include allene, 1,2-butadiene, 1,2-pentadiene, 1,2-octadiene, 4-phenyl-1,2-butadiene and the like.

The reaction of the inventive method is carried out in an inert solvent. Suitable organic solvents are exemplified by hydrocarbon solvents such as benzene, toluene, xylene and the like and ether solvents such as dibutyl ether, tetrahydrofuran and the like. The inert solvent is used in a volume preferably in the range from 100 to 1000 ml per mole of the metallic sodium.

The reaction of the inventive method is carried out by first dispersing the metallic sodium in the inert organic solvent followed by the introduction of the starting 1,2-alkadiene, either gaseous or liquid, into the reaction mixture which is a dispersion of the metallic sodium in the inert solvent. It is necessary that the metallic sodium is dispersed in the solvent as finely as possible to have a particle diameter of not exceeding 1000 $\mu$m or, preferably, not exceeding 500 $\mu$m. In order to facilitate the dispersion of the metallic sodium in the solvent, it is advisable that a dispersion aid such as oleic acid, stearic acid and the like is added to the solvent in an amount, for example, from 0.1 to 1.0 g/liter.

The procedure for dispersing the metallic sodium in the solvent is not particularly limitative and the metallic sodium may be divided in advance into particulate form and then added to the solvent. It is convenient and advantageous in general, however, that the metallic sodium is added to the solvent and heated in the solvent to a temperature above the melting point of sodium, i.e. 99.7° C., and the thus molten metallic sodium is vigorously agitated so as to be dispersed in the solvent. By this procedure, a finely divided dispersion of metallic sodium can be obtained having a particle diameter as fine as 5 $\mu$m or finer.

The starting 1,2-alkadiene is then introduced into the dispersion of the metallic sodium in the inert solvent kept at 50° to 130° C. either by adding dropwise or by blowing under agitation. The introduction of the 1,2-alkadiene may be carried out under atmospheric pressure so that no pressurizable vessel, e.g. autoclave, is necessary. As the 1,2-alkadiene is introduced into the reaction mixture, the desired reaction product, i.e. the sodium salt of the 1-alkyne, is formed in the reaction mixture as suspended in the solvent.

In the above reaction according to the invention, the yield of the desired product based on the metallic sodium is increased with the decrease of the particle diameter of the metallic sodium dispersed in the solvent to give an approximately stoichiometric result. On the other hand, a coarser particle diameter of the metallic sodium than 500 $\mu$m or, in particular, than 1000 $\mu$m results in an impracticably low yield of the desired product.

The reaction temperature is in the range from 50° to 130° C., or, preferably, in the range from 80° to 110° C.

This is because a temperature lower than 50° C. naturally cannot give a sufficiently high reaction velocity while a temperature higher than 130° C. does not give any additional advantageous effects.

The rate of introduction of the starting 1,2-alkadiene into the reaction mixture is of some significance, though dependent on several parameters such as the reaction temperature, kind of the starting diene, fineness of the sodium dispersion, etc., and it is usually in the range from 3 to 20 m moles per minute per mole of the metallic sodium dispersed in the solvent.

In accordance with the method of the invention, the desired sodium salt of the 1-alkyne can be obtained by the reaction under atmospheric pressure without using an autoclave in a high yield. The sodium salt of the 1-alkyne as the product of the inventive method is readily converted to the corresponding 1-alkyne by hydrolysis, which in turn is useful as an intermediate compound for the synthetic preparation of various kinds of perfumes, medicines, agricultural chemicals and the like.

In the following, the method of the invention is described in further detail by way of examples.

EXAMPLE 1

Into a flask of 500 ml capacity were introduced 11.5 g (0.5 mole) of metallic sodium, 200 ml of xylene and 0.05 g of oleic acid and, after replacement of the air in the flask with nitrogen, the mixture was heated up to 110° C. to melt the metallic sodium. The thus molten metallic sodium was dispersed in the solvent by agitating the mixture. The particle size of the dispersed metallic sodium was varied in five grades as indicated in Table 1 below by adjusting the intensity and the length of time of the agitation.

Into the thus prepared dispersion of metallic sodium in xylene kept at 100° to 110° C., 1,2-butadiene was blown under agitation at a rate of 4.5 m moles per minute for a length of time as indicated in Table 1. The desired sodium butynylide was immediately formed in the reaction mixture. Blowing of the starting 1,2-butadiene was terminated when no trans-2-butene was detected in the vent gas.

After completion of the above reaction, water is added to the reaction mixture to hydrolyze the sodium butynylide into ethylacetylene and the yield of the sodium butynylide was calculated from the amount of this ethylacetylene and expressed on the base of the amount of the starting metallic sodium assuming that the hydrolysis of sodium butynylide into ethylacetylene was complete. The thus calculated yield of sodium butynylide was shown in Table 1.

TABLE 1

| Experiment No. | Particle diameter of dispersed metallic sodium, μm | Blowing duration of 1,2-butadiene, hours | Yield of sodium butynylide, % based on metallic sodium |
|---|---|---|---|
| 1 | 20 to 50 | 2.8 | 96 |
| 2 | 50 to 100 | 3.0 | 93 |
| 3 | 200 to 500 | 3.5 | 86 |
| 4 | 600 to 1000 | 4.2 | 59 |
| 5 | 1000 to 5000 | 5.0 | 22 |

EXAMPLE 2

Into a flask of 500 ml capacity were introduced 11.5 g of metallic sodium, 200 ml of xylene and 0.05 g of oleic acid and the metallic sodium was melted by heating and dispersed by agitation into particles having a diameter of 20 to 50 μm.

The thus obtained dispersion of metallic sodium was kept at a temperature of 100° to 110° C. with agitation and 83 g of 1,2-octadiene were added dropwise into the dispersion taking about 3 hours. After completion of addition of 1,2-octadiene, the reaction mixture was further agitated for 1 hour while being kept at the same temperature.

The sodium octynylide formed in the reaction mixture was hydrolyzed in the same manner as in the preceding example and converted to 54 g of 1-octyne. The yield of the sodium octynylide calculated from the amount of 1-octyne was 98% assuming that the hydrolysis of the sodium octynylide into 1-octyne was complete.

What is claimed is:

1. A method for the preparation of a sodium salt of a 1-alkyne represented by the general formula

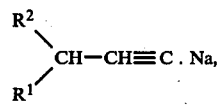

in which $R^1$ and $R^2$ each denote a hydrogen atom or a monovalent hydrocarbon group free from aliphatic unsaturation, which comprises the steps of:
   (a) adding metallic sodium to an inert organic solvent,
   (b) heating the metallic sodium in the inert organic solvent at a temperature higher than the melting point of the metallic sodium with agitation to form a dispersion of the molten metallic sodium in a finely divided form having a particle diameter not exceeding 500 μm, and
   (c) admixing a 1,2-alkadiene represented by the general formula

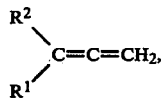

in which $R^1$ and $R^2$ each have the same meaning as defined above, with the dispersion of the molten metallic sodium in the inert organic solvent.

2. The method of claim 1 wherein the dispersion of the molten metallic sodium in the inert organic solvent contains a dispersion aid in an amount of from 0.1 to 1.0 g/liter.

3. The method of claim 2 wherein the dispersion aid is oleic acid or stearic acid.

4. The method as claimed in claim 1 wherein the reaction of the 1,2-alkadiene and the metallic sodium is carried out under atmospheric pressure.

* * * * *